US005496282A

United States Patent [19]
Militzer et al.

[11] Patent Number: 5,496,282
[45] Date of Patent: Mar. 5, 1996

[54] APPARATUS AND METHOD TO STABILIZE A PERITONEAL DIALYSIS CATHETER

[76] Inventors: George G. Militzer; Leslie H. Militzer, both of 1402 Carleton Sq., San Diego, Calif. 92106

[21] Appl. No.: 353,931

[22] Filed: Dec. 12, 1994

[51] Int. Cl.⁶ .......................... A61M 25/02; A61M 39/00
[52] U.S. Cl. .................... 604/179; 128/DIG. 26
[58] Field of Search .................. 604/174, 179, 604/180; 128/DIG. 26

[56] References Cited

U.S. PATENT DOCUMENTS

| | | | |
|---|---|---|---|
| 4,548,200 | 10/1985 | Wapner | 128/DIG. 26 |
| 4,569,348 | 2/1986 | Hasslinger | 604/179 |
| 4,591,356 | 5/1986 | Christie | 604/179 |
| 4,955,867 | 9/1990 | Endo | 604/179 |
| 4,988,338 | 1/1991 | Taylor | 604/180 |
| 5,048,512 | 9/1991 | Turner et al. | 604/179 |
| 5,205,832 | 4/1993 | Tuman | 604/179 |
| 5,342,317 | 8/1994 | Claywell | 604/179 |
| 5,352,209 | 10/1994 | Bird et al. | 604/179 |

OTHER PUBLICATIONS

1 Page Brochure for Immobile Catheter by TNT Moborg, undated.
OG Jun. 27, 1978 pp. 1395 & 1396 Showing Abstract (Claim) for U.S. Pat. No. 4,096,863.
OG May 1, 1984 p. 239 Showing Claim for U.S. Pat. No. 4,445,894.

*Primary Examiner*—Paul J. Hirsch
*Attorney, Agent, or Firm*—George T. Parsons

[57] ABSTRACT

A belt for stabilizing an implanted peritoneal dialysis catheter exiting from the abdomen of a user and having a valve at one end. The belt includes a body of elasticized fabric designed to encircle the patient, two fasteners with hook and pile features, and a receptacle. In addition, a relatively small adhesive-backed member, having adhesive on its inner surface and having a pile member on its outer surface, surrounds a portion of the catheter tubing at a point near where the tubing exits the user. One of the two fasteners secures and stabilizes the tubing to the belt body by pressing against the pile outer surface of the adhesive-backed member and subsequently is secured to itself. The second fastener is used to further secure the tubing against the belt body at a distance from the one fastener. The receptacle, or envelope, integral to the belt body, is used to securely hold the valve end of the catheter against the belt body. The method of using the present invention is also described.

19 Claims, 2 Drawing Sheets

APPARATUS AND METHOD TO STABILIZE A PERITONEAL DIALYSIS CATHETER

BACKGROUND OF THE INVENTION

1. Field of the Invention

The present invention relates generally to belt-like articles of clothing, and more particularly to a stretchable and adjustable belt which holds a peritoneal dialysis catheter device stable against a user, thereby virtually preventing any trauma to an exit site from which the catheter device extends out of the user's body.

2. Description of the Related Art

Dialysis is a way of cleaning the blood when a person's kidneys can no longer perform their function. Not long ago, total kidney failure meant death. Today, there are almost 200,000 people with end-stage kidney disease in the United States alone. They are being kept alive because of treatments such as dialysis and kidney transplant. Dialysis substitutes for the kidneys by removing the body's wastes, which include excess salt and water. Dialysis also helps control blood pressure. Two basic methods of dialysis exist: hemodialysis and peritoneal dialysis. In the hemodialysis method, blood is pumped out of the body to an artificial kidney machine which contains a special membrane to filter the blood and remove wastes. The cleansed blood is then returned to the body by tubes that connect the patient to the machine. The hemodialysis procedure takes approximately four hours and must be performed three times a week. Although hemodialysis is effective at removing wastes from the blood, patients are traumatized by the procedure. They often feel exhausted for a day or more afterwards, at which point it's time to repeat the procedure.

Peritoneal dialysis is the other method of dialysis. In this method, the wastes are filtered out of the blood across a lining of the patient's abdominal cavity. The lining is called the peritoneum and serves as a natural filtering membrane. In peritoneal dialysis, wastes are removed by means of a sterile cleansing fluid which is washed in and out of the abdomen in cycles. A soft plastic tube called a catheter is surgically placed in the patient's lower abdomen. The cleansing fluid enters the abdomen through the catheter. Wastes from the blood pass through the peritoneal membrane into the cleansing fluid. Later, when the filtering process is completed, the fluid leaves the body through the catheter.

Another name for peritoneal dialysis is "Continuous Ambulatory Peritoneal Dialysis" (CAPD). The process of CAPD does not require the patient to use a dialysis machine, and may be performed at home, at the work place or anywhere where a calm and semi-sterile environment can be temporarily established. Out of the 600,000 patients worldwide who are being treated with dialysis, a significant number, approximately 100,000, use CAPD. Patients can personally perform the procedure by placing approximately two liters of cleansing fluid in their abdominal cavity and later draining it. The procedure begins by attaching a solution container and a drain bag (two flexible plastic bags) to the catheter in the patient's abdomen through a connecting length of tubing. Raising the solution container to shoulder level causes the force of gravity to pull the solution into the abdominal cavity. While the person goes about everyday activities, wastes and excess water pass from the patient's blood stream through the network of tiny blood vessels in the peritoneal membrane and into the solution. When the CAPD is completed, an empty plastic drain bag is lowered to a surface below the abdomen. Then the solution, which now contains wastes, drains by gravity from the abdominal cavity back into the bag. The used containers are then thrown away. This process usually is performed four times during any 24-hour period while the patient is awake. Each exchange takes about 30 minutes to complete.

Compared to hemodialysis, CAPD offers several advantages. With the continuous dialysis, the patient does not have large fluid gains which may reduce stress on the heart and blood vessels. Fewer dietary restrictions are required and a need for certain medications is decreased. No long interruptions in daily activities occur and patients find work and travel arrangements much easier to perform. However, there are some difficulties with peritoneal dialysis. For example, patients on peritoneal dialysis are constantly inconvenienced by the long plastic tube, generally about two feet in length, exiting from their lower abdomen. The exit site in the abdomen is easily irritated by the tube being tugged and moved as the person moves. These injuries occur daily and cause problems ranging from simple pain and discomfort to severe infections and peritonitis. If not treated promptly peritonitis can lead to death.

The problem area is in supporting the catheter tubing. Unfortunately, to date, there has been no satisfactory way to support this tube that has been commercially available. Tape is a good temporary solution but, over time, tends to really irritate the skin. Some patients have even required medical treatment because skin breakdown was so severe. Burnnet (Systenet™) is used on many users who cannot tolerate tape but that also can be uncomfortable and expensive for long-term use.

When a catheter is poorly supported it becomes a nuisance and an annoyance. More importantly, when a catheter is dangling it is more prone to traumatic injury. This can lead to exit site complications and infection which may require medical intervention. In extreme cases the trauma has caused the need for catheter replacement, a full fledged surgical procedure.

In an attempt to overcome these difficulties mentioned above, and to help eliminate serious medical risk, inventors have tried to design devices to restrain the tubing from movement. Kaplan U.S. Pat. No. 4,096,863 discloses a band and various straps for anchoring a catheter to the body. Unfortunately, Kaplan's device is unnecessarily complicated, and is cumbersome to wear under street clothing. In addition, a rigid clip applied to the belt-like device interferes with comfort, restful sleeping and needlessly adds additional time to each 30 minute dialysis procedure. In each procedure, the Kaplan device must be totally unfastened before the catheter transfer set valve can be used. Kovacs, in U.S. Pat. No. 4,445,894 illustrates a band strapped to the body utilizing two opposing Velcro TM™-like fasteners to restrain the catheter. While Kovacs has devised a simpler solution to Kaplan's method, it is not optimized because the catheter easily slides back and forth when used for peritoneal dialysis, causing trauma to the exit site. Endo's U.S. Pat. No. 4,955,867 teaches a belt-like device incorporating a pouch to hold the valve end of the catheter. However, serious trauma to the exit site results because the approximately two foot length of tubing remains unsecured. Therefore, the dangling tubing is tugged and moved by the wearer, stressing the exit site. Furthermore, the pouch is fastened on top of the belt material making Endo's device unnecessarily thick. To applicants' knowledge, the Endo device product has not been produced and is not commercially available, presumably because of the aforementioned problems.

Finally, U.S. Pat. Nos. 4,976,700 and 5,098,399 teach a catheter and tubing immobilizer. However, this invention is inadequate for several reasons. While it immobilizes the tubing at the exit site, it leaves the valve end dangling and unprotected. It is for one-time use only, must be disposed of after use, and causes irritation and allergic reaction on the user's skin because of the adhesive tape backing that is used to secure the device to the skin.

Therefore, with all the above noted problems, there; is still an urgent and continuing need for an improved apparatus and method to stabilize a peritoneal dialysis catheter, without causing trauma to the user at the exit site.

SUMMARY OF THE INVENTION

The above-mentioned difficulties and problems of the prior art are overcome by the present invention. Briefly stated, the present invention provides novel improvements to a belt for stabilizing a peritoneal dialysis catheter device against a user. In summary, the present invention represents a soft, adjustable, elasticized belt which provides easy and quick access to a peritoneal catheter device allowing multiple and trauma-free daily dialysis fluid exchanges. Additionally, the present invention is a simple device which is comfortably worn 24 hours a day, and is used virtually always without having to disrobe.

More specifically, the present invention includes a belt body which encircles a user without slipping, an adhesive-backed fabric band attached to the tubing of the catheter device, a first fastener attaches over the adhesive-backed band to firmly stabilize the tubing to the belt body near where the tubing exits the user, a second fastener to further stabilize the tubing against the belt body, and a pocket for securely holding the valve end of the catheter device against the belt body.

One of the advantages of the adhesive-backed band is in providing stability during draining and filling, preventing stress and tugging on the tubing, thereby ensuring additional protection of the exit site. More specifically, the medical advantage of the belt is that it keeps the catheter tubing immobile at the exit site, where the tube exits the peritoneum, and protects the exit tunnel from trauma, including inadvertent dangling of the catheter device. These advantages reduce the chance of pain, exit site infections, and potentially serious peritoneal complications.

Having two fasteners, instead of one which other prior art devices have used, provides a doubly firm grip on the catheter tubing. The belt body is advantageously assembled from two pieces and, by overlapping these parts in the manufacture of the device, the two parts form a smooth pocket or envelope. The valve end is stored and protected in the envelope.

For dialysis patients with sensitive skin, protection from frequent use of tape adhesives and allergic reactions is achieved by eliminating the need of having to tape the peritoneal catheter or any part of the tubing to the skin.

Additional advantages of the preferred embodiment include the belt being manufactured from a woven and elastic material, thereby providing slight compression to abdominal bloat while it still remains expandable and adjustable to allow for bloat. The belt promotes more natural activity by allowing a full range of motion which improves patient strength and general health. Additionally, the belt is adaptable for use during most sporting activities, at night while asleep, and while bathing. It fits compactly under all normal clothing, is machine washable, durable and reusable. Wearing the belt will avoid user discomfort and complications, thereby reducing the need for medical attention and the related costs.

The method for using the present invention begins with placing the belt around one's waist. Next the belt body is positioned so that the first fastener is located approximately above the exit site. After a short loop is made in the tubing, it is placed parallel to the belt and atop the first fastener. Then the adhesive-backed band is secured around the tubing in the vicinity of the first fastener. A flap in the first fastener is then placed over the tubing and squeezed together, thereby securing the tubing firmly adjacent to the belt body. Next the valve end of the catheter is inserted into the pocket. Lastly, a second flap on the second fastener is secured over the tubing in a similar fashion as the first fastener. These, and other, features and advantages of the present invention are set forth more completely in the accompanying drawings and the following description.

BRIEF DESCRIPTION OF THE DRAWINGS

Details of the invention, and of the preferred embodiment thereof, will be further understood upon reference to the drawings, wherein closely related elements have the same number but different alphabetical suffixes, and further wherein.

DETAILED DESCRIPTION OF THE PREFERRED EMBODIMENT

Figure 1:
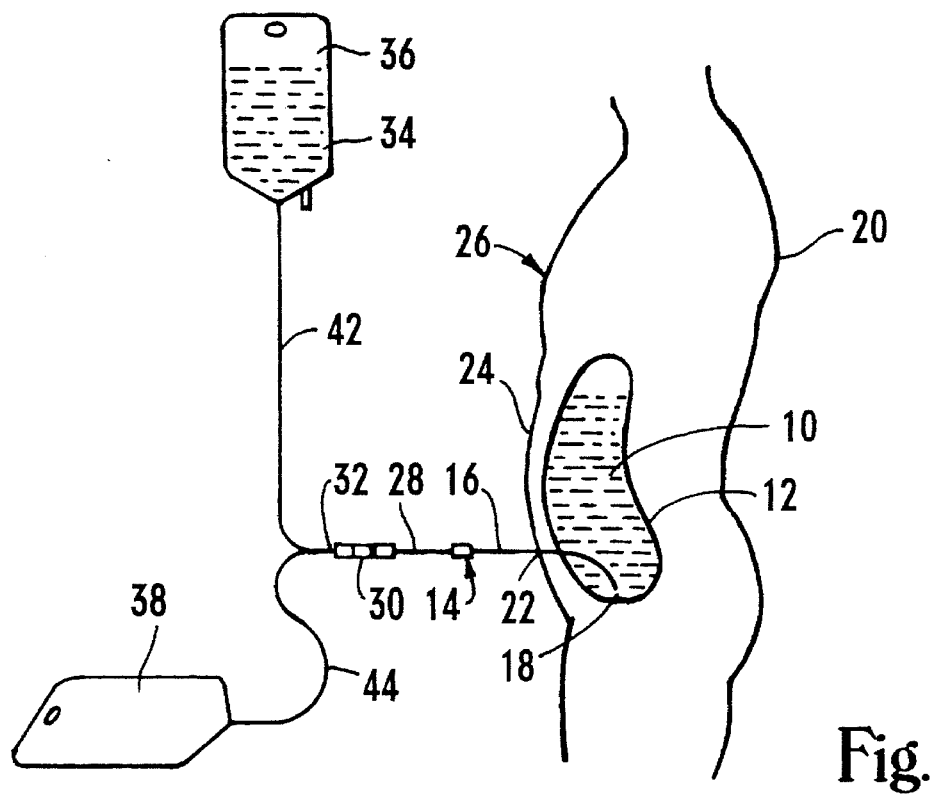
FIG. 1 is a schematic representation showing the drain and fill procedure during a peritoneal dialysis exchange from a person's abdomen.

Referring initially to FIG. 1, a schematic representation view illustrates a peritoneal dialysis procedure known as a Continuous Ambulatory Peritoneal Dialysis (CAPD) exchange. In a CAPD, waste fluid (10) is drained from a person's peritoneal cavity (12) through an implanted catheter apparatus (14), such as manufactured by the Baxter Healthcare Corporation. The CAPD process is well understood in the field of dialysis. Nevertheless, it is helpful to briefly describe each of the components of the catheter apparatus (14) prior to the subsequent discussion and description of the present invention.

Beginning from the abdominal cavity (12), catheter tubing (16), at a proximal end (18) of the catheter apparatus (14), extends from the peritoneal cavity (12) out of a person's body (20) through an exit site (22) in the outer surface (24) of the abdomen (26). The next portion of the catheter tubing (16) is designated as transfer set tubing (28). A connector (29) joins the catheter tubing (16) to the transfer set tubing (28). The transfer set tubing (28) is fixedly connected to a transfer set valve (30) at a distal end (32) of the catheter apparatus (14). The transfer set valve (30) is used to either 1) allow fresh peritoneal fluids (34) from a fill bag (36) to enter the abdominal cavity (12) through the catheter tubing (16), or 2) to allow peritoneal waste fluid (10), which now includes body wastes, to flow out of the abdominal cavity (12) into an expandable drain bag (38). Filling the peritoneal cavity (12) with fresh peritoneal fluid (34) from a flexible fill bag (36) is accomplished by first elevating the fill bag (36) above the peritoneal cavity (12). Then gravity is used to allow the fluid (34) to flow. The fresh fluid (34) flows from the fill bag (36) into the peritoneal cavity (12) when a clamp (not shown) is released from the fill bag tubing (42). The draining process of the used peritoneal fluid begins by connecting the transfer valve (30) to drain bag tubing (44). Next, the drain bag (38) is placed below the level of the peritoneal cavity (12) to allow the force of gravity to drain the waste fluid (10) out of the peritoneal cavity (12). The waste fluid (10) begins flowing when another clamp (not shown) is released from the drain bag tubing (44).

Figure 2:
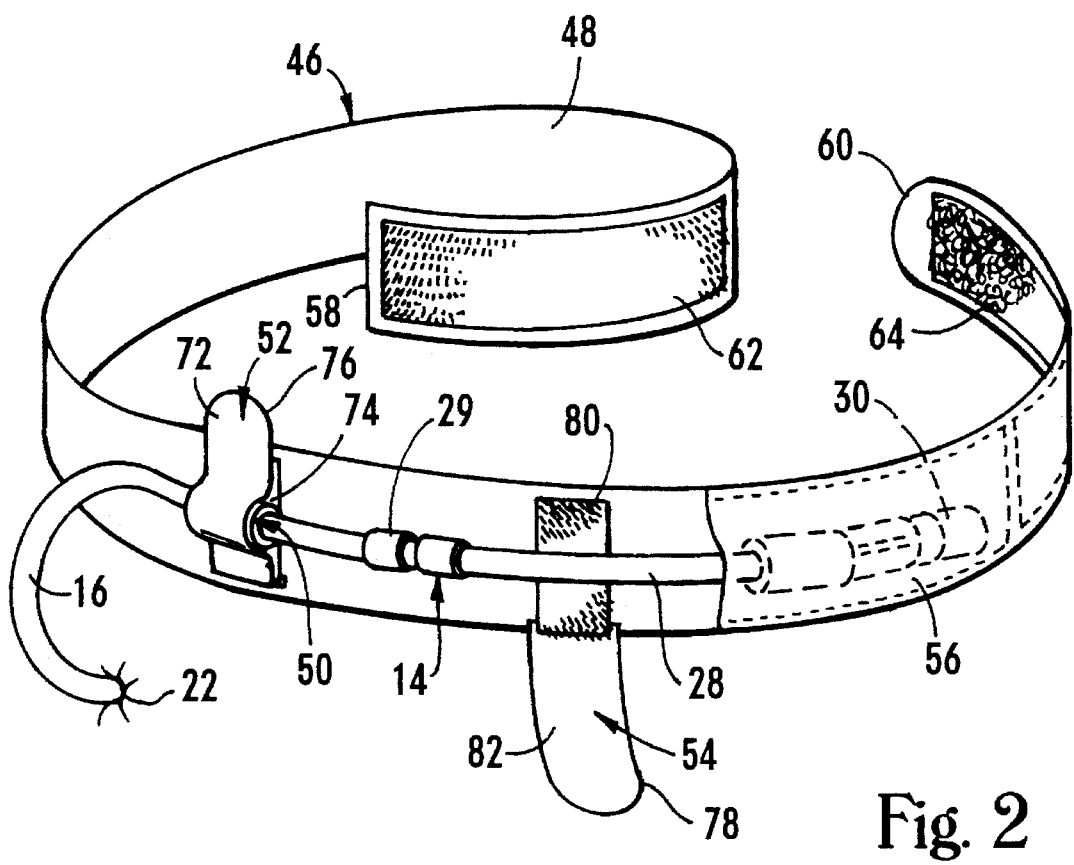
FIG. 2 is a perspective representation of the belt constructed in accordance with the concepts of the present invention, illustrating the belt holding a peritoneal dialysis catheter device.

Referring next to FIG. 2, a perspective representation view shows a portion of the representative catheter apparatus (14) being stabilized by a preferred embodiment of a belt apparatus (46). The belt (46) includes a belt body (48), an adhesive-backed band (50) semi-permanently attached to the tubing (16) of the catheter (14), a first fastener (52) attached over the adhesive-backed band (50) holding the catheter apparatus (14), a second fastener (54) to hold the catheter (14) against the belt body (48) at a point spaced from the first fastener (52), and a receptacle (56) spaced from the first (52) and second fasteners (54) for securely holding the transfer set valve (30) against the belt body (48). Together, the first fastener (52), the second fastener (54) and the receptacle (56) at the distal end (32) of the catheter apparatus (14) are radially spaced along the belt body (48) to hold the catheter apparatus (14) substantially parallel to the belt body (48).

The belt body (48) is preferably fabricated from elasticized fabric adapted to encircle a user without slipping from the user's abdomen (26). Furthermore, the belt body (48) has soft, flexible, expandable and stretchable properties, with a first end (58) and a second end (60). The belt body (48) is also adjustable using hook (62) and pile (64) closures. Such hook and pile features on material are typically incorporated in the product known as Velcro™. The hook (62) and pile (64) closures are placed at opposing end surfaces of the belt body (48) to accommodate a catheter (14) exiting on either the right or the left side of the user's body (20). To secure the belt body (48) around a user, the user merely presses the two hook and pile closures (62,64) against each other at a comfortable circumference, thereby achieving closure, of the belt body (48). The width of the belt body (48) is preferably about two inches. Experimentation has shown that a two inch width provides an optimized comfort width and prevents rolling of the fabric against the body (20) as normal daily activities occur. The belt body (48) may be of various lengths, depending on the circumference of the abdomen of different users. Preferably, the lengths could be about 20–30 inches, 26–36 inches, 30–40 inches, 34–44 inches and 40–50 inches. These lengths generally correspond to child, small, medium, large, and extra large sizes.

The first and second fasteners (52, 54) are formed into clamping devices which may be fabricated from one of numerous materials. Just some of these materials are plastic, rubber, metal and fabric. The first fastener (52) has a first flap (72) adapted to fold over the catheter tubing (16) of the catheter apparatus (14). The first fastener (52) is in secure contact with the pile outer surface (70) of the cylindrical adhesive-backed band (50). Subsequently, the first fastener attaches securely upon itself, thereby firmly stabilizing the catheter tubing (16) against the belt body (48). It is a key advantage of the present invention for the tubing (16) of the catheter (14) to be secured to the belt body (48) at a point proximate to where the tubing (16) of the catheter (14) exits the user. The first flap (72) also has a first inner surface (74) and a first outer surface (76), with the first inner surface (74) having hook fabric. The outer surface (76) is pile fabric.

The second fastener (54) is attached to the belt body (48) at a medial point along the tubing (16) of the catheter apparatus (14). Similarly to the first fastener (52), the second fastener (54) has a second flap (78) adapted to fold over the transfer set tubing (28) and subsequently attaches securely upon itself. With the use of a second fastener (54), further stabilization is achieved for the tubing (16) against the belt body (48). Again, similar to the first flap (72) on the first fastener (52), the second flap (78) has an inner (80) and an outer (82) surface. The second inner surface (80) also has hook fabric (84), while the second outer surface (82) is pile fabric as well.

The receptacle (56) is pocket-shaped, integrally attached to the belt body (48). The receptacle (56) forms an envelope so that the transfer set valve (30) is manually insertable into the envelope. The receptacle (56) is also preferably fabricated from the same fabric as the body belt (48). The length of the receptacle (56) generally conforms to the length of the transfer set valve (30), while the width of the receptacle (56) conforms generally to the dimensions of the belt body (48).

Figure 3:
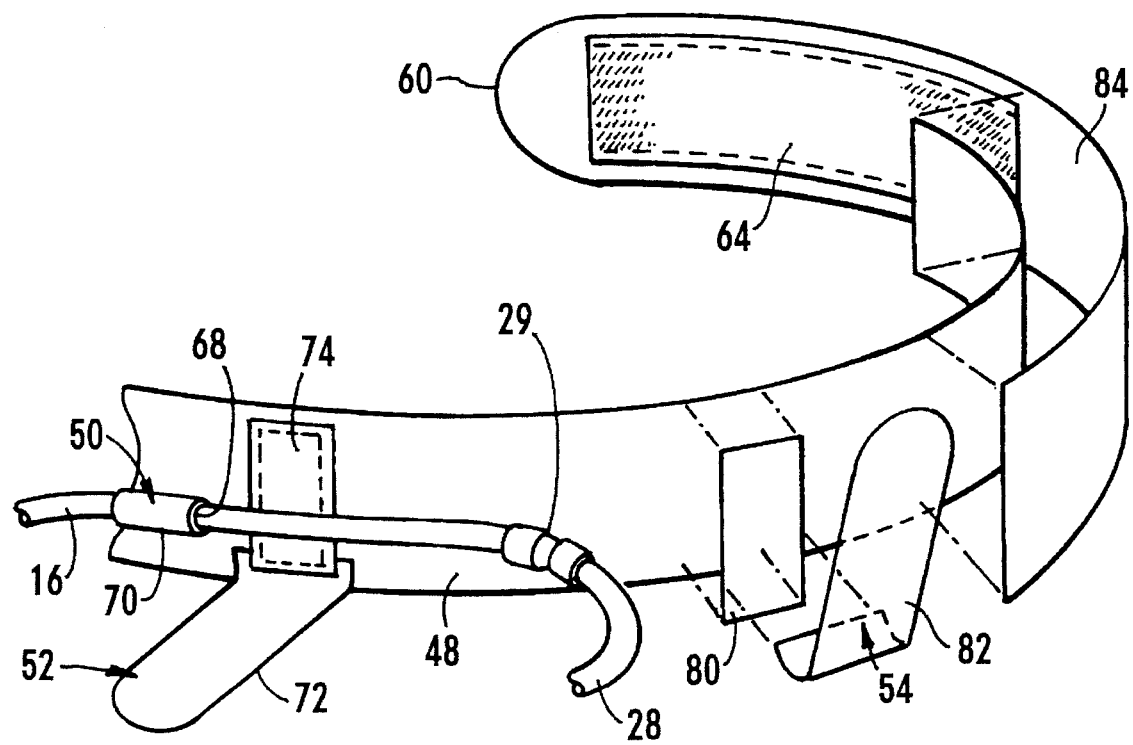
FIG. 3 is a detail perspective representation of the belt's construction; including a cut away portion of a peritoneal dialysis catheter device.

Now referring to FIG. 3, a perspective representation view shows the construction details of the belt (46). An overlap (84) of fabric which forms the belt body (48) is illustrated which forms the receptacle (56), creating the protective envelope for storage of the transfer set valve (30) while the valve (30) is not in use during an exchange. Also illustrated are the construction details of the first (52) and second (54) fasteners. More clearly illustrated in FIG. 3 are the first flap (72) of the first fastener (52) and the first inner surface (74). Also shown are details of the second inner surface (80) of the second fastener (54) and the second outer surface (82). Similarly, the second fastener (54) has a second hook tab (90) and a second pile tab (92).

The adhesive-backed band (50) has an inner (68) and outer (70) surface. The band (50) is preferably fabricated from fabric available under the Velcro™ label. The inner surface (68) of the band (50) is adhesive-backed. A key aspect in achieving stability of the catheter apparatus (14) is attaching the inner surface (68) of the band (50) around the catheter tubing (16) in a cylindrical fashion at a distance from the proximal end (18) of the tubing (16) where the catheter tubing (16) exits the abdomen (26), and in a proximate position to the first fastener (52) on the belt body (48). The band (50) advantageously offers protection by keeping the catheter tubing (16) from any slippage or movement along the belt body (48). The band (50) also has a pile outer surface (70) which is used to further secure the catheter apparatus (14) by securely contacting the first fastener (52).

Figure 4:
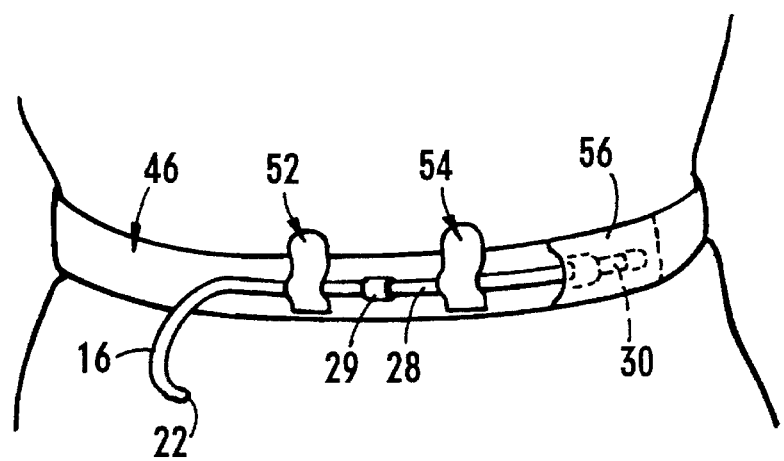
FIG. 4 is a schematic representation of the present invention illustrating the belt securing a peritoneal dialysis catheter device to a user.

Lastly referring to FIG. 4, a schematic view shows how the belt (46) is worn by a user, providing constant protection 24 hours a day to the user's exit site (22). The catheter tubing (16) is prevented from movement during sleep, work, exercise, bathing, and all other daily routine activities.

Operation

The method for using the belt (46) of the present invention includes numerous steps. Generally speaking, the belt (46) is placed around the user, the two fasteners (52, 54) are secured over the catheter tubing (16), and the transfer set valve (30) is inserted into the receptacle (56). More specifically, the first step is placing the belt (46) around one's waist. The second step is positioning the belt body (48) so that the first flap (72) of the first fastener (52) is located approximately above the exit site (22). Then the next step is making a short flexible loop with the proximal end (18) of the catheter tubing (16). Next, the tubing (16) is placed parallel to the belt (46) and atop the first fastener (52), leaving the flexible loop in the tubing (16). Now, the adhesive-backed band (50) is secured around the tubing (16) in the vicinity of the first flap (72) so that the adhesive-backed inner surface (68) of the band (50) is in firm contact around the tubing (16).

Continuing the method, the first flap (72) is overlaid on the tubing (16). Now, the first flap (72) and the tubing (16) are squeezed together with thumb and index fingers, thereby securing the tubing firmly adjacent to the belt body (48) atop the hook and pile outer surface (70) of the adhesive-backed band (50). Next, the first flap (72) is attached again to the first fastener (52). The next to last step is inserting the transfer set valve (30) of the catheter (14) inside the receptacle (56).

Lastly, the second flap (78) of the second fastener (54) is closed over the tubing (16). Using this method, the belt (46) is worn unobtrusively under normal street clothing.

Additionally, a user pinches the first flap (72) at the bottom portion of the first fastener (52), thereby snugging up the tubing (16) to prevent additional movement of the tubing (16) at the exit site (22). Also., the user pinches the second flap (78) at another bottom portion of the second fastener (54), thereby snugging up the tubing (16) to further secure it against the belt body (48). To perform the dialysis exchange, street clothing is loosened at the waistband for access to the belt (46) and catheter apparatus (14). The, second fastener (54) is released and the transfer set valve (30) is withdrawn from the receptacle (56). These steps release sufficient length of the tubing (16) for the transfer set valve (30) to be attached to the dialysis drain bag (38). Normal manufacturers' instructions and patients' medical training procedures are followed. Due to the design of the belt (46), the exit site (22) remains undisturbed during the entire process. After the exchange is completed, the user reverses steps to re-secure the catheter apparatus (14) to the belt body (48), the valve (30) is reinserted in the receptacle (56), and street clothing is readjusted.

The present invention prevents the many problems associated previously with CAPD No longer does the user experience tugging, pulling, or excess manipulation of the catheter (14) at the peritoneal exit site (22). Therefore, no longer is the tissue at the surgical implant site irritated, inflamed and damaged. With the development of the belt (46), a situation is corrected to which previously there was no good alternative. The belt (46) is designed in such a way as to totally support the catheter (14) so it is no longer hanging and dangling. It is anchored securely to prevent trauma to the exit site (22). The belt (46) ends the need to use tape which causes skin irritation. Even when sleeping or showering, the belt (46) provides complete stabilization of the catheter tubing (16).

Accordingly, it will be appreciated that the present invention can be used 24 hours a day to protect the patient from injury to the catheter exit site (22). Improved health and comfort as well as medical cost savings will accrue when infections are decreased. The belt (46) is economical and inexpensive in that it is reusable for several months. It is comfortable enough to become an integral item of apparel. It also will be understood by those skilled in the art that since peritoneal catheter insertions are implanted into the body (20) on either side, the belt (46) will be manufactured in left or right side versions.

While a particular embodiment of the invention has been described, all patients having an abdominal catheter (14) may benefit from this product. For example, as advanced materials become available or as surgical techniques change modifications may be made to improve the user's comfort by improving this product. Consequently, while the foregoing description has described the principle and operation of the present invention in accordance with the provisions of the patent statutes, it should be understood that the invention may be practiced otherwise as illustrated and described above and that various changes in the size, shape, and materials, as well as on the details of the illustrated construction may be made, within the scope of the appended claims without departing from the spirit and scope of the invention.

What is claimed is:

1. An apparatus for stabilizing an implanted peritoneal dialysis catheter, having a valve at a distal end, said catheter at a proximal end having tubing exiting from the abdomen of a user, comprising:

(a) a belt body of elasticized fabric adapted to encircle a user without slipping;

(b) an adhesive-backed fabric band semi-permanently attached to said tubing of said catheter;

(c) a first fastener attached to said adhesive-backed band to firmly secure and stabilize said tubing of said catheter to said belt body at a point proximate to where said tubing of said catheter exits the user;

(d) a second fastener to hold said catheter against said belt body at a point spaced from said first fastener; and (e) a receptacle spaced from said first and said second fasteners for securely holding said valve against said belt body.

2. The apparatus according to claim 1, wherein said belt body has a first end and a second end, further comprising hook and pile fastener material at said first and second ends of said belt body to fasten said belt about the patient.

3. The apparatus according to claim 1, wherein said adhesive-backed band is attached in cylindrical fashion around said tubing of said catheter at a proximal end.

4. The apparatus according to claim 3, wherein said adhesive-backed band is further comprised of a pile outer surface.

5. The apparatus according to claim 1, wherein said first fastener further comprises a first flap adapted to fold over said tubing of said catheter, pressing against said adhesive backed fabric band, and subsequently attaching securely upon itself, thereby firmly stabilizing said tubing against said belt body.

6. The apparatus according to claim 5, wherein said first flap further comprises a first inner and a first outer surface, wherein said first inner surface is further comprised of first hook and pile members, and said first outer surface is fabric.

7. The apparatus according to claim 1, wherein said second fastener is attached to said belt body at a medial point along said tubing of said catheter, said second fastener further comprising a second flap adapted to fold over said tubing and subsequently attaching securely upon itself, thereby further stabilizing said tubing against said belt body.

8. The apparatus according to claim 7, wherein said second flap further comprises a second inner and a second outer surface, wherein said second inner surface is further comprised of second hook members, and said second outer surface is pile fabric.

9. The apparatus according to claim 1, wherein said receptacle comprises a receptacle, integrally attached to said belt body, said valve being insertable into said receptacle.

10. The apparatus according to claim 1, wherein said first and said second fasteners and said receptacle are longitudinally spaced along said belt body to hold said catheter substantially parallel to said belt body.

11. The apparatus according to claim 1, wherein said fasteners are formed from a clamping device fabricated of plastic.

12. The apparatus according to claim 1, wherein said fasteners are formed from a clamping device fabricated of rubber or any rubber like material.

13. The apparatus according to claim 1, wherein said fasteners are formed from a clamping device fabricated of metal.

14. The apparatus according to claim 1, wherein said fasteners are formed from a clamping device fabricated of fabric.

15. The apparatus according to claim 1, wherein said belt body is preferably about two inches in width.

16. The apparatus according to claim 1, wherein said belt body may be one of various lengths, depending on the circumference of the abdomen of different users.

17. The apparatus according to claim 16, wherein said lengths are preferably at least one of: 20–30 inches, 26–36 inches, 30–40 inches, 34–44 inches and 40–50 inches.

18. A method for using said apparatus of claim 6, comprising the steps of:

placing said belt body around one's waist;

positioning said belt body so that said first flap of said first fastener is located approximately above said exit site;

making said short flexible loop with said proximal end of said tubing;

placing said tubing, leaving said flexible loop in said tubing, parallel to said belt and atop said first fastener;

securing said adhesive-backed band around said tubing in the vicinity of said first flap so that said adhesive-backed inner surface of said band is in firm contact around said tubing;

overlaying said first flap over said tubing;

squeezing said first flap and said tubing together with thumb and index fingers, thereby securing said tubing firmly adjacent to said belt body atop a hook and pile outer surface of said adhesive-backed band and attaching said first flap again to said first fastener;

inserting said valve end of said catheter inside said pocket; and closing said second flap of said second fastener over said tubing.

19. The method according to claim 18 for using said apparatus, further comprising the steps of:

pinching said first flap at a bottom portion of said first flap, thereby snugging up said tubing to prevent movement of said tubing of said catheter at said exit site; and pinching said second flap at another bottom portion of said second flap, thereby snugging up said tubing to further secure said tubing to said belt body.

* * * * *